US009504616B2

United States Patent
Belsinger, Jr. et al.

(10) Patent No.: US 9,504,616 B2
(45) Date of Patent: Nov. 29, 2016

(54) INFANT PATIENT TRANSFER DEVICE WITH HEART RATE SENSOR

(71) Applicant: General Electric Company, Schenectady, NY (US)

(72) Inventors: Harry Edward Belsinger, Jr., Forest Hill, MD (US); Steven Mitchell Falk, Baltimore, MD (US); Thomas Charles Underwood, Sykesville, MD (US); Karen P. Starr, Monkton, MD (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/483,315

(22) Filed: Sep. 11, 2014

(65) Prior Publication Data

US 2016/0074260 A1   Mar. 17, 2016

(51) Int. Cl.
*A61B 5/02* (2006.01)
*A61G 1/048* (2006.01)
(Continued)

(52) U.S. Cl.
CPC .............. *A61G 1/048* (2013.01); *A47D 13/02* (2013.01); *A61B 5/0245* (2013.01); *A61B 5/02438* (2013.01); *A61B 5/0402* (2013.01); *A61B 5/04085* (2013.01); *A61B 5/6892* (2013.01); *A61B 5/702* (2013.01); *A61B 5/7278* (2013.01); *A61B 5/7282* (2013.01); *A61B 7/04* (2013.01); *A61B 8/02* (2013.01); *A61G 1/00* (2013.01); *A61B 5/742* (2013.01); *A61B 2503/045* (2013.01); *A61G 1/04* (2013.01);
(Continued)

(58) Field of Classification Search
CPC .. A61G 1/048; A61B 5/0245; A61B 5/1115; A61B 2503/04; A61B 2503/045; A61B 2505/01; A61B 5/002; A61B 5/006; A61B 5/655; A61B 5/603; A61B 5/94
USPC ............ 600/301, 27–28, 21–22, 523; 5/655; 604/174; 340/539.11–539.12
See application file for complete search history.

(56) References Cited

U.S. PATENT DOCUMENTS

| 4,066,072 A | 1/1978 | Cummins |
| 6,687,523 B1 * | 2/2004 | Jayaramen ......... A41D 13/1281 |
| | | 600/388 |

(Continued)

FOREIGN PATENT DOCUMENTS

EP   1627597 A1   2/2006

OTHER PUBLICATIONS

International Search Report and Written Opinion for PCT/US2015/046539, mail date Nov. 17, 2015, 12 pages.

*Primary Examiner* — Paula J Stice
(74) *Attorney, Agent, or Firm* — Andrus Intellectual Property Law, LLP

(57) ABSTRACT

A patient transfer device is utilized to transport infant patients between locations within a hospital environment. The patient transfer device includes a center, support section and a pair of side sections that can be moved into contact with each other to surround the infant patient. The first and second side sections each include a handle that can be brought into close proximity to each other and can be grasped by a single hand of a clinician. The patient transfer device includes a heart rate sensor positioned to provide a heart rate measurement of the patient when the patient is received on the patient transfer device. The patient heart rate can be displayed on either an integrated display or wirelessly transmitted to an external display device. In this manner, the heart rate of the infant can be continuously monitored during transport.

12 Claims, 4 Drawing Sheets

(51) Int. Cl.
*A61B 5/0245* (2006.01)
*A61B 5/0402* (2006.01)
*A61B 5/00* (2006.01)
*A61B 7/04* (2006.01)
*A47D 13/02* (2006.01)
*A61G 1/00* (2006.01)
*A61B 8/02* (2006.01)
*A61B 5/024* (2006.01)
*A61B 5/0408* (2006.01)
*A61G 1/04* (2006.01)
*A61G 11/00* (2006.01)

(52) U.S. Cl.
CPC .......... *A61G 11/00* (2013.01); *A61G 2200/14* (2013.01); *A61G 2200/327* (2013.01); *A61G 2203/30* (2013.01); *A61G 2203/46* (2013.01)

(56) References Cited

U.S. PATENT DOCUMENTS

| | | | |
|---|---|---|---|
| 2002/0019296 A1* | 2/2002 | Freeman | A63F 13/02 482/4 |
| 2004/0236174 A1 | 11/2004 | Boone et al. | |
| 2006/0169282 A1* | 8/2006 | Izumi | A61B 5/08 128/204.23 |
| 2007/0149883 A1 | 6/2007 | Yesha | |
| 2010/0241018 A1* | 9/2010 | Vogel | A61B 5/0002 600/511 |
| 2013/0116514 A1* | 5/2013 | Kroner | A61B 7/00 600/301 |
| 2013/0340770 A1 | 12/2013 | Starr et al. | |
| 2015/0045608 A1* | 2/2015 | Karp | A61M 21/02 600/28 |

\* cited by examiner

INFANT PATIENT TRANSFER DEVICE WITH HEART RATE SENSOR

BACKGROUND

The present disclosure generally relates to a device for moving an infant patient. More specifically, the present disclosure relates to an infant patient transfer device (sling) that can be used to support an infant patient during movement while providing a heart rate reading from the infant when the infant is within the patient transfer device.

Presently, the standard practice used to transfer an infant patient out of an incubator or bed is for a nurse or other care physician to carefully slide a hand (or two) under the infant patient and manually lift the patient. When the nurse physically contacts the infant patient, the patient is often stimulated which, in high risk patients, can introduce unwanted stress to the infant patient. In addition, when a nurse lifts the infant patient, there is an increased risk of the nurse snagging one or more of the multiple lines connected to the patient (IV, EKG leads, ET tube, etc.). The possibility of snagging or disconnecting tubes connected to the infant patient can increase the risk to the infant patient during the lifting procedure.

In order to address these problems, a patient transfer device, such as shown in U.S. Patent Publication No. 2013/0340770 was developed. When a patient is received within the infant patient transfer device, the patient is securely held in place for transport. Currently, there is a trend to delay clamping of the umbilical chord after the baby has been born. In such situations, the infant may be held within the patient transfer device for between one and ten minutes. While the infant is within the patient transfer device, there is no monitoring of the patient vital signs, including heart rate. Once the infant is transported to an infant warmer, patient bed or incubator, sensors are applied to the patient to begin monitoring vital signs.

According to neonatal resuscitation guidelines issued by the American Heart Association and the American Academy of Pediatrics, nearly all of the decision points regarding the possible need for resuscitation of an infant are based upon the heart rate of the infant. Currently, there is no form of continuous heart rate measurement available immediately after birth. Instead, heart rate monitoring begins once the infant is received within a patient monitoring device, such as an incubator, warmer or infant bed.

SUMMARY

The present disclosure relates to a patient transfer device for moving, an infant patient. The patient transfer device securely holds the patient and includes a heart rate sensor that detects the heart rate of the infant for display either on the patient transfer device or at a remote display.

The patient transfer device includes a center support section that is positioned beneath the patient First and second side sections are each connected to the center support section. The first side section includes a first handle while the second side section includes a second handle. When an infant patient is supported on the center support section, the first and second side sections can be moved upward and toward each other such that the first and second handles are positioned in close proximity to each other. When the first and second handles are positioned in close proximity to each other, the clinician can grasp both of the first and second handles with a single hand to move the patient while the patient is supported by the patient transfer device.

The patient transfer device further includes a stiffening device that can be positioned within the center support section to provide rigid support for the infant patient during movement. In one embodiment of the disclosure, the stiffening device is a backboard that is received within a pocket formed in the center support section. The backboard can be selectively removed and inserted onto the center section as needed and desired. The backboard preferably extends along a longitudinal axis, wherein the backboard is flexible along the longitudinal axis and rigid in a direction transverse to the longitudinal axis. The rigid nature of the backboard supports the patient's spine during movement while allowing the first and second side sections to move toward each other to securely envelope the patient during transport.

The patient transfer device may further include a hold down device positioned on one of the first and second side sections. The hold down device receives and retains the wires and tubes connected to the patient such that the wires and tubes are securely retained during transport of the patient. Various types of hold down devices are contemplated as being within the scope of the present disclosure. One embodiment includes a section of material that can be connected to the second side section to hold the tubes and wires in place.

The patient transfer device may further include a heart rate sensor positioned within the center support section. The heart rate sensor is designed to sense the heart rate of an infant when the infant is supported along the center support section.

The patient transfer device can further include an integrated display that receives a heart rate signal from the heart rate sensor. The integrated display on the patient transfer device displays the sensed heart rate, which allows a caregiver to monitor the heart rate of the infant when the infant is supported on the patient transfer device. The integrated display can be designed to indicate the heart rate of the baby while the baby is either resting upon the center section or being carried by a caregiver.

In addition to including an integrated display, the patient transfer device can be configured to include a wireless transmitter to transmit heart rate signals to a remote display. The wireless transmitter can be configured to transmit information to a remote display, such as on an infant warmer, incubator or other type of infant bed. In this manner, the patient transfer device can be positioned within the infant bed and can transmit heart rate information to the infant bed either continuously or on a real-time, regular basis.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
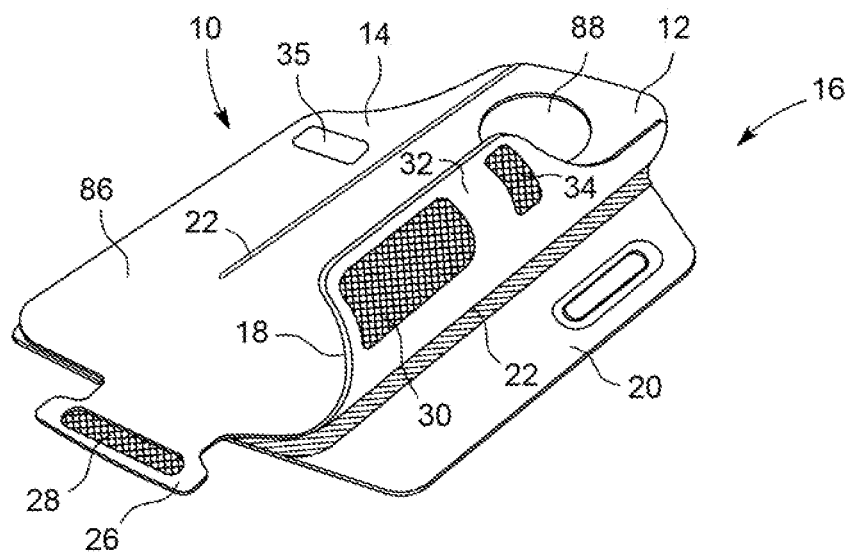
FIG. 1 is a front perspective view of a first embodiment of a patient transfer device of the present disclosure.

FIG. 1 illustrates a patient transfer device 10 of the present disclosure. The patient transfer device 10 can be used to transfer an infant patient from one location to another while minimizing the physical contact between the clinician and the patient while providing secure support for the patient during movement.

Figure 2:
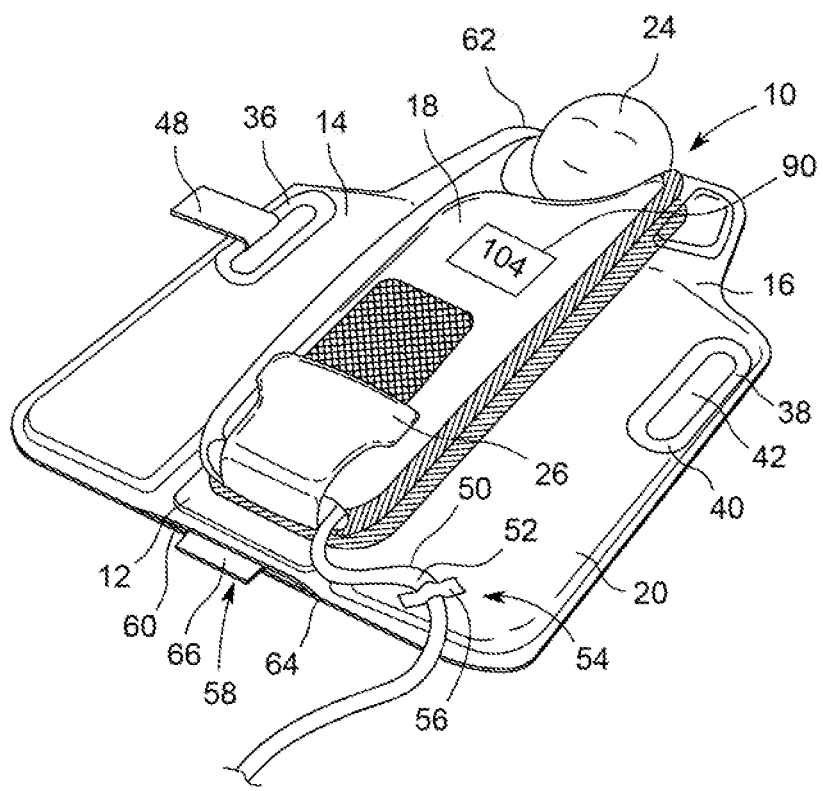
FIG. 2 is a front perspective view of the first embodiment of the patient transfer device with an infant supported on the device.

As illustrated in FIG. 1, the patient transfer device 10 includes a center section 12, a first side section 14 and a second side section 16. In the embodiment illustrated in FIG. 1, the patient transfer device includes an inner liner 18 and an outer liner 20 that each form portions of the center side sections. Although an inner liner 18 and an outer liner 20 are shown as separate components in FIG. 1, it should be understood that the inner and outer liners 18, 20 could be combined as a single layer that forms the center section 12 and the first and second side sections 14, 16. In the embodiment shown in FIG. 1, the inner liner 18 is formed from a soft, foam material, and is joined to the outer liner 20 along a pair of spaced attachment lines 22. The outer liner 20 can be formed from a slightly more rigid and durable material as compared to the inner liner 18. As illustrated in FIG. 2, infant patient 24 can be placed on the inner liner 18 and the opposite sides of the inner liner 18 that forms a portion of the side sections folded over the patient 24 to surround the patient as illustrated.

In the embodiment shown in FIG. 1, the inner liner 18 includes an extended end portion 26 that includes an end fastener 28. When the patient is supported on the inner liner as shown in FIG. 2, the end fastener 28 formed as part of the end portion 26 is received along a second fastener 30. In the embodiment shown in FIGS. 1 and 2, the fasteners 28, 30 are opposite portions of a hook and loop fastener, such as Velcro®. The physical engagement between the fasteners 28, 30 allows the end portion 26 to fold the inner liner 18 in the condition shown in FIG. 2. Although a hook and loop fastener are shown in the embodiment of FIGS. 1 and 2, it should be understood that different types of fasteners could be utilized while operating within the scope of the present disclosure. Alternatively, the end portion 26 could be eliminated while also operating within the scope of the present disclosure.

Referring back to FIG. 1, the fastener 30 is secured to an inner surface 32 of the inner liner 18 and is exposed only after the second side section of the inner liner is wrapped around the infant patient. In addition to the fastener 30, an upper fastener portion 34 is also positioned along the inner surface 32. The upper fastener portion 34 is engaged by a mating fastener 35 formed along the first side section 14 of the inner liner 18. The fasteners 34, 35 can also he mating portions of a hook and loop fastener, such as Velcro®. The fasteners 34, 35 aid in holding the first and second side sections of the inner liner 18 in the condition shown in FIG. 2. Although hook and loop fasteners are shown in the embodiment of FIGS. 1 and 2, it should be understood that other types of fasteners could be utilized while operating within the scope of the present disclosure.

As illustrated in FIG. 2, the portion of the outer liner 20 that forms a portion of the first side section 14 includes a first handle 36 while the portion of the outer liner 20 that forms a portion of the second side section 16 includes a second handle 38. In the embodiment shown in FIG. 2, the first and second handles 36, 38 are formed only in the outer liner 20 and are defined by a plastic outer housing 40 that forms an open interior 42.

Figure 3:
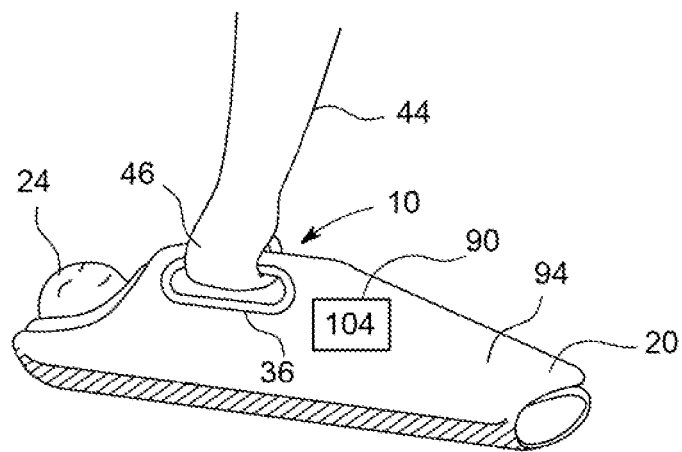
FIG. 3 is a view illustrating the use of the transfer device to move an infant patient.

As can be seen in FIG. 3, when the infant patient 24 is supported along the transfer device 10, a clinician 44 can grasp the pair of handles 36, 38 with a single hand 46 and lift the infant patient for transport and movement. As can be understood in FIGS. 2 and 3, the first and second side sections 14, 16 are sized such that the first and second handles 36, 38 are located close enough to each other to facilitate grasping of the entire patient transfer device 10 by the single hand 46.

Referring back to FIG. 2, in the embodiment illustrated, a strap 48 can be attached to one of the first and second handles 36, 38 and used to secure the handles together during transport of the patient 24. Although a flexible strap 48 is shown in FIG. 2, various other types of straps could he utilized while operating within the scope of the present disclosure. Alternatively, the strap 48 could he eliminated.

Figure 4:
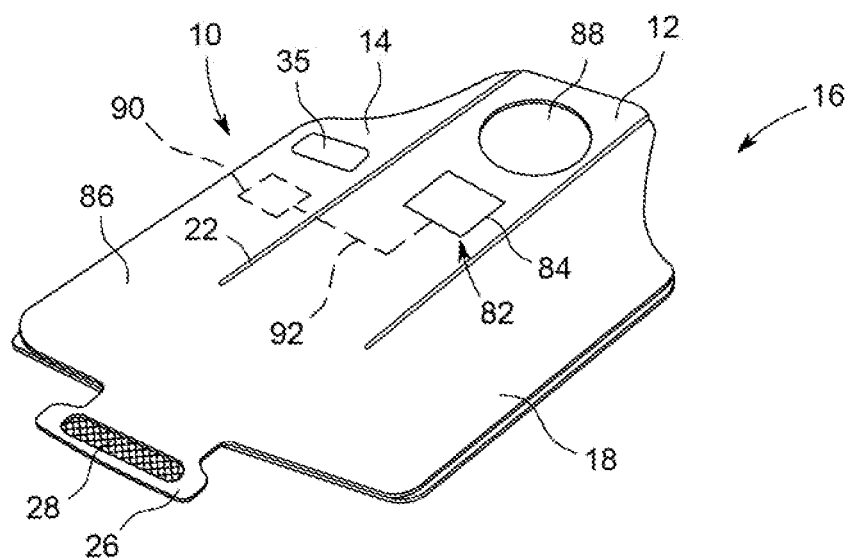
FIG. 4 is a front perspective view similar to FIG. 1 illustrating the position of one embodiment of a heart rate sensor and an integrated display.

As illustrated in FIG. 2, a series of tubes 50 and wires 52 are often attached to the patient 24 that needs to be transported. Since the wires and tubes 50, 52 are often inserted into the patient or connected at specific locations on the patient, it is desirable not to disrupt the tubes and wires during movement. Thus, a need exists for some type of hold down device to prevent the tubes and wires from being disconnected from the patient 24 during transport. In the embodiment shown in FIG. 2, a hold down device 54 is formed on one of the first and second side sections 14, 16 of the transport device. In the embodiment of FIG. 4, a section of adhesive tape 56 is attached to the inner surface of the outer liner 20 in the second side section 16. Although adhesive tape 56 is shown in FIG. 2, other types of hold down devices 54 are contemplated as being within the scope of the disclosure. For example, the hold down device 54 could be a section of a hook and loop fastener, a strap with a button on snap, a section of flexible material or any other type of device that could be utilized to hold the tubes and wires 50, 52 in a secure position as illustrated.

In the embodiment shown in FIG. 2, a stiffening device 58 is shown inserted into a pocket 60 formed in the center section 12 of the patient transfer device 10. The stiffening device 58 typically extends the entire length of the center section 12 from the first end 62 near the patient's head to a second end 64 near the feet of the patient The stiffening device 58 provides the required stiffness for the patient transfer device 10 such that when the patient transfer device 10 is used to support the patient the stiffening device 58 prevents the first and second side sections 14, 16 from collapsing onto the patient 24. Additionally, the stiffening device 58 provides the required stiffness for the transfer device 10 such that the transfer device and the patient do not collapse in the longitudinal direction between the first end 62 and the second end 64.

In the embodiment shown in FIGS. 1 and 2, the stiffening device 58 is a backboard that is received within the pocket 60 and extends the entire length of the patient transfer device 10 from the first end 62 to the second end 64. The backboard 66 is preferably formed from a plastic material that has the required stiffness, durability and size to provide the required support for the infant patient 24. Although plastic is described as being the most preferred material for the backboard 66, it is contemplated that other materials could be utilized while operating within the scope of the present disclosure.

Alternatively, the removable stiffening device 58 and sewn-in pocket 60 could be replaced with other types of stiffening devices. As an example, a series of inflatable tubes could be formed within the center section 12 and selectively inflated/deflated depending upon whether the patient 24 is on the transfer device 10 and needs to be moved. Various other types of stiffening devices are also contemplated as being within the scope of the present disclosure. The use of the stiffening device 58 is contemplated as being valuable to provide secure and stable support for the infant patient 24 during movement.

Figure 5:
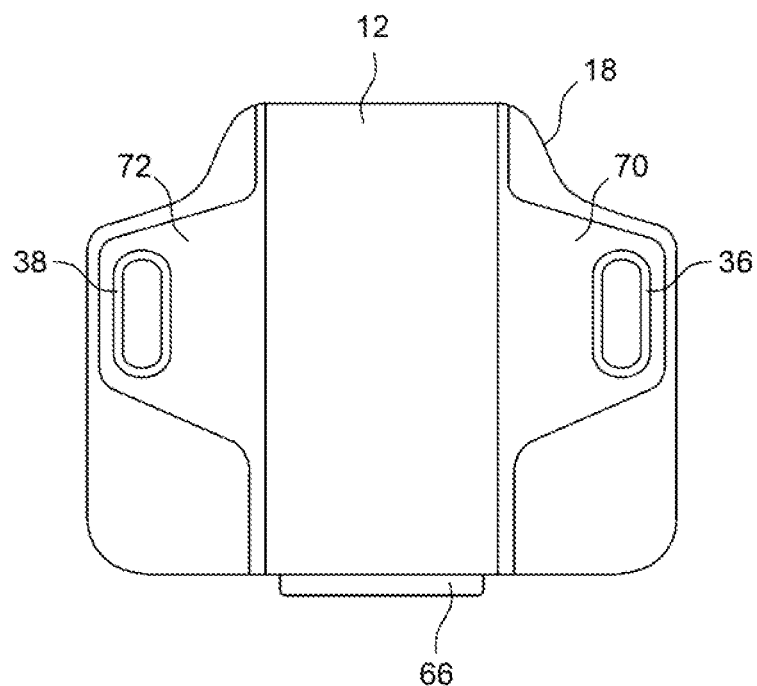
FIG. 5 is a back view of an alternate embodiment of the patient transfer device.

FIG. 5 illustrates a second embodiment of the patient transfer device 10 of the present disclosure. In the second embodiment shown in FIG. 5, the stiffening device 58 is also a backboard 66 that can be moved into and out of a pocket formed in the center section 12. In the embodiment shown in FIG. 5, the first side section 14 includes the inner liner 18 and a smaller, outer liner 70. Likewise, the second side section 16 includes the inner liner 18 and smaller, outer liner 72. The outer liners 70, include the first and second handles 36, 38 as in the first embodiment shown in FIGS. 1-2.

Figure 6:
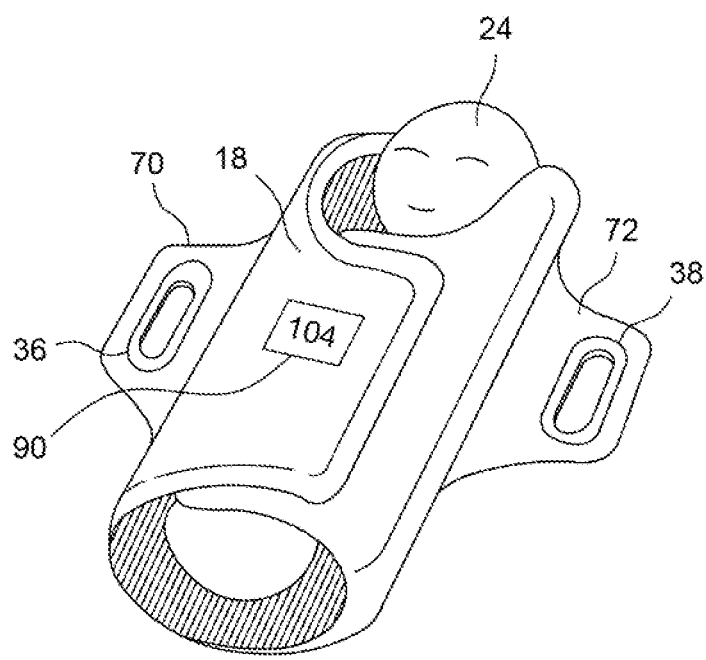
FIG. 6 is a view of the alternate embodiment of the patient transfer device used to support an infant patient.
Figure 7:
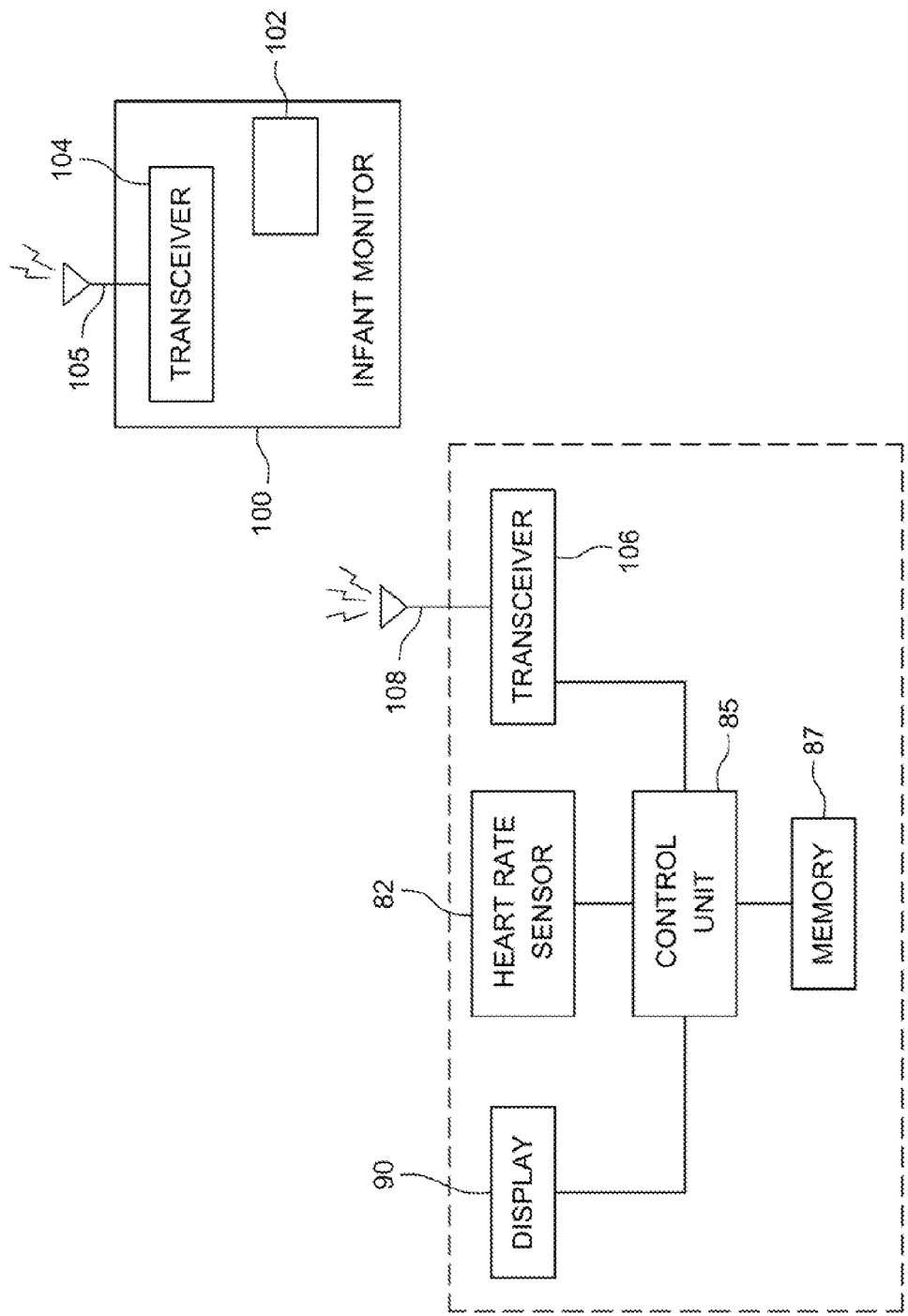
FIG. 7 is a schematic illustration showing the communication between the heart rate sensor, integrated display and a remote display utilizing a wireless transmission device.

As illustrated in the back view of FIG. 5, the outer liner sections 70, 72 are joined to the center section 12. As in the first embodiment, the inner liner 18 is formed from a soft, foam material that provides a comfortable support surface for an infant patient when the infant patient is supported on the inner liner 18. As illustrated in FIG. 6, the patient 24 is supported along the center section and the inner liner of both the first and second side sections are wrapped around the patient 24. Although not illustrated, it is contemplated that various types of fastening devices and materials could be utilized to hold the opposite sides of the inner liner 18 in place as shown. When the patient 24 is wrapped within the inner liner 18 as illustrated, the outer liner sections 70, 72 of the first and second side sections can be brought together such that a single hand 46 of the clinician 44 can be used to grasp both handles, as illustrated in FIG. 7.

As shown in FIG. 4, the patient transfer device 10 further includes a heart rate sensor 82 that is positioned within the center section 12. In the embodiment shown in FIG. 4, the heart rate sensor 82 is graphically depicted as a patch or pad 84 that is positioned within the center section 12. However, it is contemplated that various different types of heart rate sensors 82 could be utilized while operating within the scope of the present disclosure and could be positioned in other locations on the patient transfer device 10. Detailed below are several possible examples of different types of heart rate sensors that could be utilized while operating within the scope of the present disclosure.

In a first embodiment of the disclosure, the heart rate sensor 82 determines the heart rate of the infant using an electrical signal obtained from the infant. In one example, an electrical signal can be obtained by placing a series of ECG sensor strips or pad along the surface of the inner layer 18 in the center section 12. The ECG sensor strips or pads are located within the center section and pick up ECG signals from the infant. Each of the strips or pads is typically a silver impregnated area located on the sling material that obtain ECG signals from the infant. The bean rate sensor 82 is shown in the embodiment of FIG. 4 as connected to an integrated display device 90 through a communication line 92. The integrated display device 90 can either include an integrated processor and memory device or can be in communication with a separate control unit 85 and memory device 87, as shown in FIG. 7. Although a separate memory device 87 is shown, it is contemplated that the memory device 87 could be incorporated into the control unit 85. In either case, the memory device 87 can be loaded with an algorithm that calculates the heart rate of the infant based upon the ECG signals obtained from the heart rate sensor 82. As an example, the algorithm can be configured to calculate the heart rate of the infant from R-wave intervals calculated from the ECG strips or pads. Alternatively, the algorithm can select the two ECG signals received from the multiple ECG strips or pads and measure the cardiac dipole between the two leads as a differential measurement.

In a second, contemplated alternate embodiment, the heart rate sensor 82 can determine the heart rate of the infant based upon an acoustic measurement taken from the infant in such an example, the heart rate sensor 82 could be a microphone that is buried within the sling. Although the term microphone is used, the heart rate sensor 82 utilizing an acoustic measurement could be any equivalent device that is able to generate an output signal based upon acoustic signals from the infant. The microphone buried within the sling could include a sheet of piezoelectric material that senses an acoustic signal from the infant and relays the sensed, acoustic signal to the control unit 85, as shown in FIG. 7. The control unit 85 retrieves processing algorithms from the memory device 87 that calculate the heart rate of the infant based upon the acoustic signals detected by the microphone that forms the heart rate sensor 82.

In a third, contemplated alternate embodiment, the heart rate sensor 82 could be a vibration sensor positioned within the patient transfer device. As an example, the heart rate sensor could include a piezoelectric pad that contacts the skin surface of the infant and generates a measurement signal that is received by the control unit 85. The control unit 85 again retrieves a processing algorithm from the memory device 87 that calculates the heart rate of the infant based upon the vibration signals obtained from the heart rate sensor 82.

In yet a fourth, contemplated alternate embodiment, the heart rate sensor 82 could be a sensor that detects the flow of blood through veins/arteries of the patient. As an illustrative example, the heart rate sensor 82 could be an ultrasound patch or an RF patch that is positioned within the sling. If the heart rate sensor 82 were an RF or ultrasound patch, the RF or ultrasound patch is drive to generate an RF or ultrasound signal that can be used to detect the blood flow through an extremity of the patient. The sensed signal from the RF or ultrasound patch is then relayed to the control unit 85. The control unit 85 will then be able to retrieve a stored algorithm to calculate the heart rate of the patient based upon the sensed blood flow from the ultrasound or RF sensor. Once again, the control unit 85 receives the signal from the ultrasound or RF sensor and is able to calculate the heart rate of the infant.

In a fifth, alternate configuration, the heart rate sensor 82 could be a sensor that calculates the heart rate of the infant based upon a color change of the infant or upon a temperature change of the infant. As an example, the patient transfer device could include an infrared LED that detects the color change in an infant's skin. The color change signal would be relayed to the control unit 85, where the control unit can calculate the heart rate of the infant.

In each of the alternate, contemplated embodiments described above, the patient transfer device includes a heart rate sensor 82 that relays information along a communication line 92 to a control unit for processing. The control unit includes the required processing capabilities and memory to store analysis algorithms such that the control unit can calculate the heart rate of the infant based upon the signal from the heart rate sensor 82. The heart rate sensor 82 can be one of a relatively large number of heart rate sensors that can detect various different physiological parameters of the infant, which can be used to calculate heart rate. In the embodiment described above, the heart rate can be calculated utilizing one of the following: electrical signals from the infant, acoustic signals from the infant, vibrational signals from the infant, blood flow measurements from the infant or color or temperature changes from the infant. In each case, the heart rate sensor 82 and the control unit are able to generate a heart rate of the infant when the infant is contained within the patient transfer device.

In the embodiment shown in FIG. 4, the heart rate sensor 82 is shown connected to a display device 90 through a communication line 92. It is contemplated that the communication line 92 could pass beneath or through the inner liner 18 and provide wired communication between the heart rate sensor 82 and the control unit 85 of the display device 90. Alternatively, the heart rate sensor 82 and display 90 could be configured to communicate with each other using various different types of wireless communication protocols. The use of a wired connection will decrease the cost and complexity of both the heart rate sensor 82 and the display device 90.

In the embodiment shown in FIG. 3, the display device 90 is viewable from an outer surface 94 of the outer liner 20. In the embodiment illustrated in FIG. 3, the integrated display device 90 includes an LCD display configured to show at least the sensed heart rate of the infant. Thus, when the infant is being carried as shown in FIG. 3, a caregiver can view the display device 90 and determine the heart rate of the infant 24. The display device 90 is designed to continuously display the most recent heart rate of the infant determined by the heart rate sensor. The heart rate can be determined on a regular basis, such as every five seconds. Other intervals between heart rate calculations are contemplated. In each case, the most recent heart rate calculation is shown on the display device for viewing by the caregiver, In a contemplated, alternate embodiment, the display device 90 could be positioned on the inner liner 16 and thus be viewable when the infant is secured as shown in FIG. 2. In either case, the integrated display device 90 allows the caregiver to visually view the heart rate of the infant as determined by the heart rate sensor 82.

In the alternate configuration shown in FIG. 6, the display device 90 is integrated into the inner liner 18 and is viewable by the caregiver when the baby is supported on the center section and wrapped securely by the overlapping inner liners 18.

FIG. 7 is a schematic illustration showing the possible types of communication from the control unit 85 to either the integrated display 90 contained within the patient transfer device 10 or an infant monitor 100 located remotely from the patient transfer device 10, or both. It is contemplated that the infant monitor 100 could be included in various different types of infant care devices that include monitors, such as a radiant warmer, or an infant bed. The infant monitor 100 preferably includes a display 102 that can be used to display various different types of monitored physiological parameters from the infant. As an example, when an infant is placed within a radiant warmer, sensors are connected to the infant to monitor the infant's heart rate, temperature and overall weight. Each of these monitored parameters is shown on the display 102.

The infant monitor 100 is shown as including a wireless transceiver 104 and an antenna 105 that can send and receive wireless signals, such as from a transceiver 106 contained within the patient transfer device 10. The transceiver 106 includes an antenna 108 that allows the transmitter to send wireless signals for receipt by the infant monitor. It is contemplated that the wireless signals could be sent utilizing various different types of wireless protocols, such as but not limited to Blue Tooth or ZigBee. The inclusion of the wireless transceiver 106 in the patient transfer device 10 allows the heart rate sensor 82 to continue to monitor the infant heart rate and relay the signals to the infant monitor 100 when the patient transfer device 10 is positioned within the patient bed including the monitor 100. Although both the patient transfer device 10 and infant monitor 100 are described as including multi-directional transceivers, it is contemplated that the patient transfer device could only include a transmitter and infant monitor only include a receiver.

Referring back to FIGS. 1 and 2, the method of utilizing the patient transfer device 10 of the present disclosure will now be described. Although the present method is being described as one preferred method of utilizing the patient transfer device 10, it should be understood that the patient transfer device 10 could be utilized in different ways depending upon the clinician requirement and the desired amount of movement necessary for the patient 24.

Initially, the patient transfer device 10 is positioned within an incubator or patient bed before the patient is placed within the incubator or bed. It is contemplated that the patient transfer device 10 could be placed in an incubator in situations in which the patient will be moved frequently by the clinician.

Once the patient transfer device 10 is placed within the incubator, the patient is placed on the outer surface 86 of the inner liner 18 in the center section 12. In the embodiment illustrated, the inner liner 18 includes both the heart rate sensor 82 and a headrest 88 that includes additional cushioning for the patient's head. However, the headrest 88 could be eliminated while operating within the scope of the present disclosure.

When the infant is positioned on the center section 12, the heart rate sensor 82 begins to detect the heart rate of the infant. The signal from the heart rate sensor 82 is received by the control unit 85, which includes the required processing capabilities to calculate the heart rate from the heart rate sensor 82. The heart rate is calculated on a regular, real-time basis and is relayed to the integrated display device 90 where the heart rate is displayed to the caregiver. If the patient transfer device 10 is positioned near the infant monitor 100 shown in FIG. 7, the transceiver 106 will transmit the heart rate to the infant monitor 100 for display on the infant monitor display 102. If the patient transfer device is not close enough to the infant monitor 100, the transmission of the heart rate will not be relayed to an external monitor. The most recent, calculated heart rate of the infant will be displayed on the display device 90 for viewing by the caregiver.

In one contemplated embodiment, the display device could include heart rate thresholds that are either preset into the control unit 85 or entered by a caregiver based on the infant. If the sensed heart rate of the infant either exceeds the upper heart rate threshold or falls below the lower heart rate threshold, the display device could be configured to generate some type of alarm indication. Such alarm indication could be a change of color of the display, an audible warning, a flashing display or any other type of indicator that would provide a visual indication or audio indication to the caregiver that the heart rate of the infant has fallen below or above the heart rate thresholds.

When it is desired to move the patient 24, the clinician initially installs or activates the stiffening device 58 within the center section 12. In the embodiment shown in FIG. 2, the stiffening device 58 is a backboard 66 which is inserted into the open pocket 60 formed in the center section 12. Although a backboard 66 is shown in the embodiment, other types of stiffening devices could be utilized while operating within the scope of the present disclosure. It is desirable that the stiffening device 58 can be selectively removed to increase the comfort of the patient 24 if simply resting within a bed or incubator.

As described previously, it is desired that the backboard 66 be inflexible in a direction transverse to the lengthwise, longitudinal axis of the backboard 66. The rigid, inflexibility of the backboard 66 in a direction transverse to the longitudinal axis provides additional support for the back and spine of the patient during transport. However, it is also desirable that the backboard 66 be somewhat flexible toward the longitudinal axis so that when the first and second side sections are lifted over the patient, the backboard slightly flexes to increase the comfort for the patient.

Once the stiffening device 58 has been positioned in the center section 12, the inner layer that defines the first side section 14 is folded upward and into contact with the patient. Once in place, the portion of the inner layer defining the second side section 16 is folded into contact with the opposite side of the inner layer and the first and second fasteners 34, 35 engage each other to hold the inner layer in the condition shown in FIG. 2.

Once the first layer is folded into the condition shown in FIG. 2, the end portion 26 is folded upward into contact with the fastener 30. At this time, the wires and tubes leading from the patient are securely attached to the second side section 16 utilizing the hold down device 54. Although the hold down device 54 is shown positioned on the second side section 16, it should be understood that the hold down device 54 could also be on the first side section 14 or a separate hold down device included on each of the first and second side sections 14, 16.

Once the wires and tubes 50, 52 have been secured by the hold down device 54, the first and second side sections 14, 16 are brought upward toward each other until the first handle 36 and the second handle 38 are positioned near each other. Once the first and second handles are positioned near each other, the handles can be grasped by a single hand 46 of the clinician, as shown in FIG. 4.

When the first and second handles are positioned as shown in FIG. 3, the display 90 can still be viewed by the caregiver during transport of the infant. The second embodiment shown in FIG. 6 also provides a display 90 that can he viewed by the caregiver when the infant is being transported. In this manner, the caregiver can continuously keep an eve on the heart rate of the infant as the infant is carried from one location to another.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A transfer device configured to support an infant patient during transfer of the infant patient, comprising:
    a center support section configured to be postioned beneath the infant patient;
    a stiffening device positioned within the center support section and configured to provide support for the infant patient during transfer of the infant patient;
    a first side section connected to the center support section;
    a second side section connected to the center support section, wherein the first and second side sections are sized to surround the infant patient when the first and second side sections are folded toward each other when the infant patient is on the center support section;
    a heart rate sensor within the center section and configured to continuously monitor the infant patient's heart rate during transfer; and
    a display integrated into the transfer device, wherein the display is in communication with the heart rate sensor to display the infant patient's heart rate.

2. The transfer device of claim 1 wherein the heart rate sensor is in communication with a control unit contained in the transfer device, wherein the control unit calculates the infant patient's heart rate based upon a sensed signal from the heart rate sensor.

3. The transfer device of claim 1 wherein the display is configured to communicate a visual alert when the infant patient's heart rate falls outside of a predefined range.

4. The transfer device of claim 1 further comprising a wireless transmitter operatively connected to the heart rate sensor.

5. The transfer device of claim 1 wherein the display is integrated into one of the first and second side sections.

6. A transfer device configured to support an infant patient during transfer of the infant patient, comprising:
    a center support section configured to be positioned beneath the infant patient;
    a first side section connected to the center support section and including a first handle;
    a second side section connected to the center support section and including a second handle, wherein the first and second side sections are movable toward each other such that the first and second handles are located adjacent to each other and the first and second side sections surround the infant patient;
    a heart rate sensor within the center section and configured to continuously monitor the infant patient's heart rate during transfer; and
    a display integrated into the transfer device, wherein the display is in communication with the heart rate sensor to display the infant patient's heart rate.

7. The transfer device of claims 6 wherein the heart rate sensor is in communication with a control unit contained in the transfer device, wherein the control unit calculates the infant patient's heart rate based upon a signal from the heart rate sensor.

8. The transfer device of claim 7 wherein the heart rate sensor comprises at least one electrical pad comprising a plurality of ECG leads, wherein the electrical pad is positioned to monitor electrocardiograph signals from the infant patient.

9. The transfer device of claim 7 wherein the heart rate sensor comprises a microphone positioned to monitor acoustic signals from the infant patient.

10. The transfer device of claim 7 wherein the heart rate sensor comprises a vibration sensor positioned to monitor vibrations created by the infant patient.

11. The transfer device of claim 6 wherein the display is configured to communicate an alert when the infant patient's heart rate falls outside a predefined range.

12. The transfer device of claim 6 wherein the heart rate sensor is positioned within the center support section.

* * * * *